US00PP10372P

United States Patent [19]

Ebihara

[11] Patent Number: Plant 10,372

[45] Date of Patent: May 5, 1998

[54] HYDRANGEA PLANT NAMED 'FRAU TAIKO'

[75] Inventor: Hiroshi Ebihara, Ninomiya-machi, Japan

[73] Assignee: Miyoshi & Co. Ltd., Tokyo, Japan

[21] Appl. No.: 734,366

[22] Filed: Oct. 16, 1996

[51] Int. Cl.[6] ..... A01H 5/00

[52] U.S. Cl. ..... Plt./67.1

[58] Field of Search ..... Plt./67.1

[56] References Cited

U.S. PATENT DOCUMENTS

| | | | |
|---|---|---|---|
| P.P. 9,499 | 4/1996 | Ebihara | Plt./67.1 |
| P.P. 9,500 | 4/1996 | Ebihara | Plt./67.1 |
| P.P. 9,510 | 4/1996 | Ebihara | Plt./67.1 |

OTHER PUBLICATIONS

UPOVROM Disk 1997/03 Result Sheet ① GTITM UPOVROM Listing NZ PBR SHM091 Published Jul. 14, 1996.

UPOVROM Disk 1997/03 Result Sheet ② GTITM UPOVROM Listing AUPBR 96111 Filing Date May 31, 1996.

*Primary Examiner*—James R. Feyrer
*Assistant Examiner*—Kent L. Bell
*Attorney, Agent, or Firm*—James R. Cypher

[57] ABSTRACT

This invention relates to a new and distinct cultivar of *Hydrangea macrophylla* (Thunb.) named 'Frau Taiko' which originated as a seedling from the inventor's controlled hybridization of the *Hydrangea macrophylla* cultivars 'Crystal' and 'Silver Edge' and is distinguished from its parents and all other varieties of *Hydrangea macrophylla* of which I am aware by the combination of the distinctive pigmentation pattern of its sepals which gives the florets an appearance of being sharply outlined by a tiny white line; its compact growth habit; the ease with which it can be forced in a greenhouse; and its large, dense, long-lasting inflorescence having a strong peduncle which does not require staking for support, making it ideal for pot culture. Sepal pigmentation of individual *Hydrangea macrophylla* plants depends on the nutrients and pH of the growing medium. The sepals of 'Crystal' are uniformly blue and the sepals of 'Silver Edge' are uniformly red with a white edge.

2 Drawing Sheets

BACKGROUND OF THE INVENTION

This invention relates to a new and distinct cultivar of the Saxifragaceae family. The botanical name of the plant is *Hydrangea macrophylla* (Thunb.). The varietal denomination is 'Frau Taiko'. The new cultivar originated as a seedling from the inventor's controlled crossing as pollen and seed parents, respectively, the varieties known as 'Silver Edge' and 'Crystal' in Tochigi-Prefecture, Japan. 'Frau Taiko' was discovered and selected as one flowering plant within the progeny of the stated parentage in a controlled environment. 'Frau Taiko' is distinguished from its parents and all other varieties of *Hydrangea macrophylla* of which I am aware, by the combination of the distinctive pigmentation pattern of its sepals; its compact growth habit; the ease with which it can be forced in a greenhouse; and its large, dense, long-lasting inflorescence having a strong peduncle which does not require staking for support, making it ideal for pot culture.

The naturally occurring colors of Hydrangea plants are either uniformly pink, blue or white depending on the pH and nutrients of the soil. Hydrangea plants having mixed white and pink or white and blue flower coloring are relatively new and not in common use. The sepal color of 'Frau Taiko' begins uniformly green and turns color starting at the outer tips of the sepals, and at maturity is predominantly colored with a tiny border of white around the circumference of the sepal. The white border around the edge is so small and even that it gives the appearance of being a sharp outline of each sepal, and of each floret in the inflorescence. The sepal coloration of the seed parent 'Crystal' is uniformly blue, and the sepal coloration of the pollen parent 'Silver Edge' is uniformly red with a white edge.

This new cultivar has been successfully asexually reproduced by vegetative cuttings under controlled environmental conditions at a commercial nursery in Tochigi-Prefecture, Japan, under the direction of the inventor over a ten year period from 1986 to 1996, with its distinguishing characteristics remaining stable.

DESCRIPTION OF THE DRAWINGS

The accompanying drawings consist of color photographs that show the typical plant form, including the inflorescence, foliage, and unique sepal pigmentation pattern. 'Frau Taiko' is shown with either a pink and white sepal pigmentation pattern, or a blue and white pigmentation pattern. The colors are represented as truly as possible using conventional photographic procedures.

FIG. 1 is a view of the blue form of the entire plant showing its form, compact growth habit, dark green foliage, dense and large inflorescence, color and the unique appearance that the white outline of each sepal gives to the entire plant.

FIG. 2 is a close-up view of a mature sepal in the blue form illustrating the color and white outline edge.

FIG. 3 is a close-up view of one immature inflorescence illustrating that the nonsepalous buds color prior to the sepal coloration.

DESCRIPTION OF THE NEW PLANT

Figure 4:
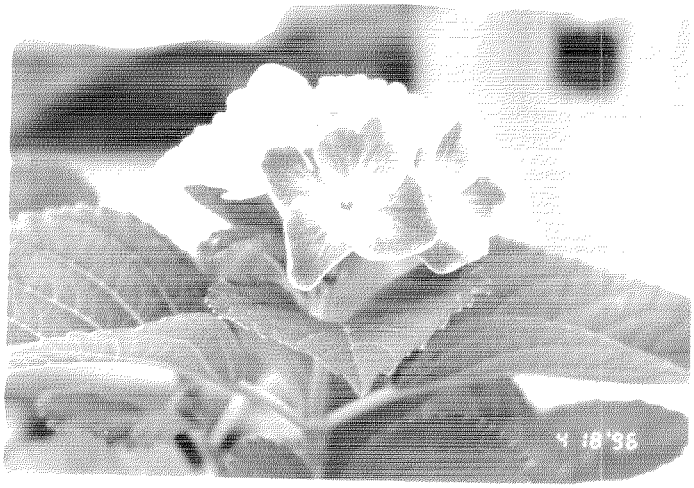
FIG. 4 is a close-up view of one immature inflorescence of the pink form the plant illustrating the development of color in the sepals and the distinct white outline.
Figure 5:
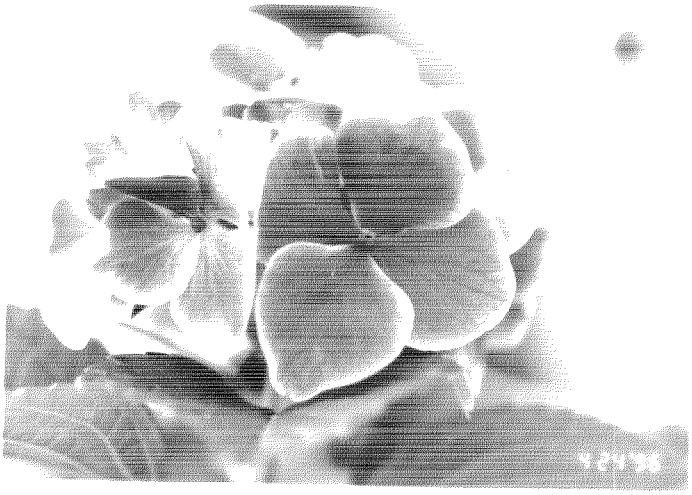
FIG. 5 is a close-up view of one mature floret in the pink form of the plant illustrating the color, and distinct tiny white outline of the floret.
Figure 6:
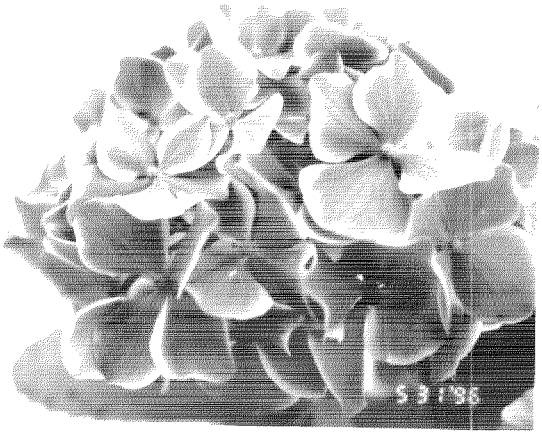
FIG. 6 is a close-up view of one inflorescence in the pink form of the plant illustrating the unique appearance that the white outline of each sepal gives to the entire inflorescence.

'Frau Taiko' has not been observed under all possible environmental conditions. The phenotype may vary significantly with variations in environment such as temperature, light intensity and day-length. The following is a detailed description of the new cultivar as forced under the prevailing day-lengths at Half Moon Bay, Calif. under commercial greenhouse conditions at a time appropriate for the sale of the cultivar in the spring. The color determinations were made with The Royal Horticultural Society (R.H.S.) Colour Chart.

The Plant

Origin: Seedling.

Parentage:

*Seed parent.*—*Hydrangea macrophylla* (Thunb) 'Crystal'.

*Pollen parent.*—*Hydrangea macrophylla* (Thunb) 'Silver Edge'.

Classification:

*Botanic.*—*Hydrangea macrophylla* (Thunb.) 'Frau Taiko'.

*Commercial.*—Florist Hydrangea 'Frau Taiko'.

Form: Upright, compact shrub.

Height: Flowering shoots reach 32 cm. in a 4" pot.

Growth: Upright, vigorous growth habit; when forced to bloom in greenhouse the addition of growth regulators is necessary to control height.

Flowerhead: Terminal; composite, rounded clusters of small florets; dome-shaped and dense; composed of florets carried on sturdy peduncles.

Stems: Lenticels are reddish on the stem; lateral buds are reddish at the tip; reddish coloration above leaf attachment sites.

Foliage: Abundant.

*Size of leaf.*—As large as 104 mm wide by 120 mm long.

*Shape of leaf.*—Elliptic with acute base and apex; margins are serrate.

*Texture.*—Glabrous; veins dominate on the underside of the leaf and are sunken on the leaf surface.

*Color.*—Upper side is R.H.S. 137 A (green group); under side is R.H.S. 138B (green group); veins are R.H.S. 145 C (yellow-green group).

*Petioles.*—33 mm long.

The Bud

Form: Globose; with 4 to 5 connate petals. Buds in the very center of the inflorescence are nonsepalous. The majority of buds have sepals. Nonsepalous buds color prior to sepal coloration.

Size: Sepalous buds 3 mm; nonsepalous buds 4 mm.

Aspect: Smooth.

Rate of opening: Buds with sepals opening more slowly than buds without sepals.

Color: Mature stage is R.H.S. 116B blue green group; green stage is 145C yellow green group.

Arrangement: Borne on 4 to 5 branched panicles, usually 5.

Inflorescence

Time of blooming: Forced in approximately 80 days at 19° C. night temperatures.

Form: Paniculate. Both sterile, sepalous florets and fertile, nonsepalous florets borne on same panicle.

Size of Inflorescence: Individual inflorescence size is dependent on the number of inflorescences per plant. The large inflorescences have been measured with a 15.5 cm diameter, and a 47 cm. circumference on a 3+ bloom plant. Usually 46 cm circumference and 15.5 cm diameter.

Shape: Spherical clusters of small florets; sepalous florets are flat and overlap one another. Sepals are persistent. Sepals elongate and mature as the inflorescence matures. Nonsepalous, are inconspicuous and hidden by sepalous florets. The inflorescence is dense.

Appearance: Showy.

Persistence: 4 or more weeks.

Fragrance: Faintly sweet.

Fruit: None.

Reproductive organs:

*Stamens.*—usually 8. Pollen is white.

*Stigma.*—2 to 4 pronged stigma; usually 2 pronged on sepalous florets and usually 3 pronged on nonsepalous florets.

Sepalous florets:

*Number of sepals.*—3 to 5 sepals per floret, usually 4.

*Aspect of sepals.*—Smooth.

*Shape of sepals.*—Reniform with acuminate apex; edges smooth — not serrated.

*Size of sepals.*—Usually one large dominate sepal; two smaller but of equal size, and one small. Largest single sepal measured 41 mm wide by 34 mm long.

*Size of one large 4 petaled floret.*—70 mm. wide by 66 mm. long.

*Coloration of sepals.*—Sepal color varies according to the soil pH and nutritional amendments supplied. The tiny white border is influenced by the dominance and closeness of the blue or pink pigmentation and does not appear to be "true white."Pink flower: R.H.S. purple violet group 82B at mature selling stage. Blue flower: R.H.S. violet group 88B at mature selling stage. Edge: R.H.S. white group 155A.

I claim:

1. A new and distinct hybrid plant variety of the Saxifragaceae family substantially as herein shown and described.

* * * * *

UNITED STATES PATENT OFFICE
PTO - BOYERS, PA DUTY STATION

---

MISSING PAGE TEMPORARY NOTICE

PATENT NUMBER PP10372 FOR THE ISSUE DATE OF 5/5/1998 HAS BEEN SCANNED, BUT CONTAINS A MISSING PAGE TEMPORARY NOTICE. UPON RECEIPT OF THE MISSING PAGE(S), THE ENTIRE DOCUMENT WILL BE RESCANNED. IF YOU HAVE ANY QUESTIONS, PLEASE CONTACT DENEISE BOYD OF THE DATA MAINTENANCE BRANCH DATA CENTER OPERATIONS DIVISION (DMB) BY E-MAIL AT HER ADDRESS DENEISEBOYD@USPTO.GOV OR BY PHONE (703) 306-3116.

THIS NOTICE IS FOR THE MISSING PAGE CONTAINING:

Drawing sheet 1

---

DATA CONVERSION OPERATION
BOYERS, PA